(12) United States Patent
Naimark et al.

(10) Patent No.: US 7,527,604 B2
(45) Date of Patent: May 5, 2009

(54) ROTATABLE MULTI-PORT THERAPEUTIC DELIVERY DEVICE

(75) Inventors: Wendy Naimark, Cambridge, MA (US); Maria Palasis, Wellesley, MA (US); Toby Freyman, Waltham, MA (US); William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 124 days.

(21) Appl. No.: 11/074,850

(22) Filed: Mar. 9, 2005

(65) Prior Publication Data

US 2006/0206062 A1 Sep. 14, 2006

(51) Int. Cl.
*A61M 31/00* (2006.01)
*A61M 37/00* (2006.01)
(52) U.S. Cl. ............ 604/95.04; 604/528; 604/264
(58) Field of Classification Search ............ 604/890.1, 604/264, 156, 528, 95.04, 93.01; 600/556; 424/449
See application file for complete search history.

(56) References Cited

U.S. PATENT DOCUMENTS

| 5,865,794 | A | 2/1999 | Castro et al. |
| 6,233,474 | B1 * | 5/2001 | Lemelson ............ 600/411 |
| 6,280,414 | B1 | 8/2001 | Shah et al. |
| 6,287,285 | B1 * | 9/2001 | Michal et al. ............ 604/264 |
| 6,663,613 | B1 | 12/2003 | Evans et al. |
| 2001/0007059 | A1 | 7/2001 | Mirzaee |
| 2002/0013615 | A1 * | 1/2002 | Haim et al. ............ 607/120 |
| 2003/0040712 | A1 | 2/2003 | Ray et al. |
| 2003/0069560 | A1 * | 4/2003 | Adamis et al. ............ 604/521 |
| 2003/0216693 | A1 | 11/2003 | Mickley |
| 2006/0051404 | A1 * | 3/2006 | Yeshurun et al. ............ 424/449 |

FOREIGN PATENT DOCUMENTS

JP 7-220394 8/1995

* cited by examiner

*Primary Examiner*—Nicholas D Lucchesi
*Assistant Examiner*—Laura A Bouchelle
(74) *Attorney, Agent, or Firm*—Vidas, Arrett & Steinkraus (57) ABSTRACT

A therapeutic delivery device is provided wherein a delivery body is supported by an elongate member such that the body may rotate as it delivers therapeutic to a target site. Therapeutic may be delivered by deploying delivery heads into a target site as well as by dispensing therapeutic from the delivery head. The delivery body may be cylindrically shaped, spherically shaped or shaped in various other configurations. In one embodiment the delivery body contains tracks that may roll back and forth over a target site to dispense therapeutic. In another embodiment, the delivery heads of the delivery body have internal valves that open and close in order to dispense therapeutic.

32 Claims, 11 Drawing Sheets

ROTATABLE MULTI-PORT THERAPEUTIC DELIVERY DEVICE

FIELD OF THE INVENTION

The present invention relates to the delivery of therapeutic to a target area. More particularly, the present invention relates to therapeutic delivery devices, methods or systems with one or more therapeutic delivery bodies that have new and unique degrees of freedom of motion.

BACKGROUND

The delivery of therapeutic to a target site is an important and often repeated practice of contemporary medicine. Target sites, where the therapeutic may need to be deposited, can be located in areas that are easily accessible as well as in areas that are more difficult to reach. When the areas are easily accessible a hand-held syringe or other hand-held device may be used to deliver the therapeutic. When the areas are not easily accessible, a remote delivery device or system may be used. These may include an endoscope working in conjunction with a catheter.

BRIEF DESCRIPTION OF THE DRAWINGS

The foregoing and further features and advantages of the invention will become apparent from the following description and the accompanying drawings, where like numerals are used to represent like elements and, wherein.

DETAILED DESCRIPTION

Embodiments of the present invention are directed to devices, methods and systems for therapeutic delivery that employ multiple therapeutic delivery heads. In some embodiments, a device, system or method may be used for delivering therapeutic and other agents or fluids to a target site of a patient's body. The device, system or method may include a rotating multi-headed delivery body where one or more therapeutic delivery heads may be able to dispense therapeutic therefrom. The dispensing end of each head may be in fluid communication with a therapeutic supply, which may be within the head and elsewhere. The) device may be used to deliver therapeutic to a target site during or subsequent to the spinning or rotation of the delivery body. These heads may pierce into the target site, may simply deposit the therapeutic and may have other defining features. These as well as other aspects of the invention are provided herein.

Figure 1:
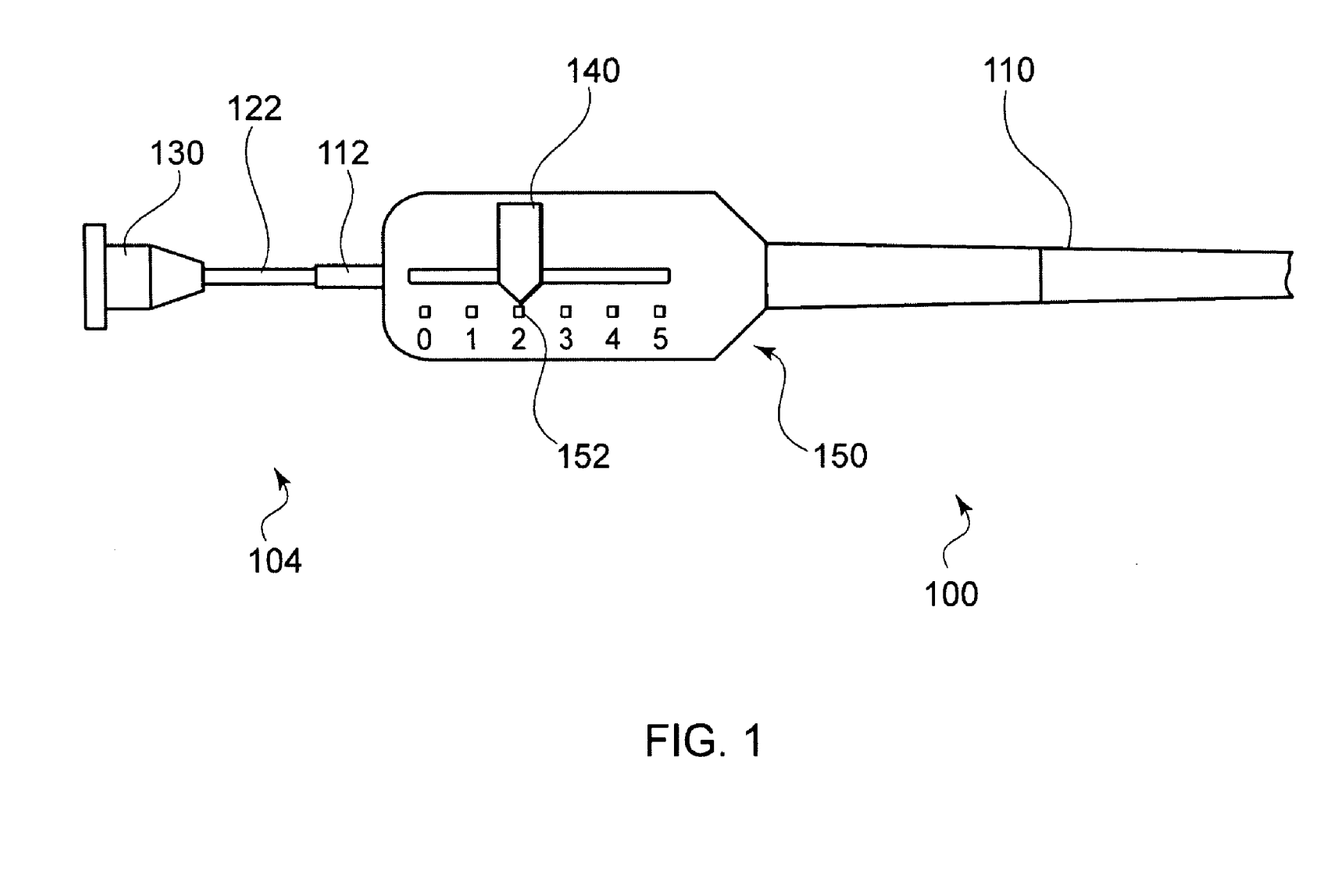
FIG. 1 is a plan view of the proximal end of a catheter that may be employed in an embodiment of the present invention.

FIG. 1 is a plan view of the proximal end of a catheter 100 that may be employed in accord with the present invention. This catheter 100 may include a housing gauge 150, a first lumen 112, a second lumen 122 with a luer fitting 130, indices 152, and pointer 140. The pointer 140 may indicate to a practitioner the distance that the second lumen 122 has slid within the first lumen. This may indicate how far the second lumen is extending from the first lumen if the second lumen is long enough to extend from the end of the first lumen. The various embodiments of the present invention may use this catheter 100 as a supply line to the rotatable delivery bodies described herein. Other sources of therapeutic may be used as well.

The shaft 110 of the catheter 100 may have a reinforcement member therein. This member may include a co-braided polymer tube, a co-extruded tube with two or more polymers, one or more rigid polymer or metallic wires and rods embedded in a polymer tube. It may also include two coaxial tubes, one being of a rigid nature, mechanically joined by, for example, a heat shrink tube over a polymer tube. The first lumen 112 and the second lumen 122 may be made of various metallic and non-metallic materials. These materials may include, but are not limited to, stainless steel and nickel-titanium alloy. Regardless of which materials are used for first the first lumen 112 and the second lumen 122, it is preferred that the materials be chosen such that they have compatible physical properties in order to be able move in a one to one relationship as the catheter 100 is snaked through a patient. This one to one relationship increases the likelihood that the movement of the second lumen within the first lumen can be accurately measured by gauge 150.

Figure 2:
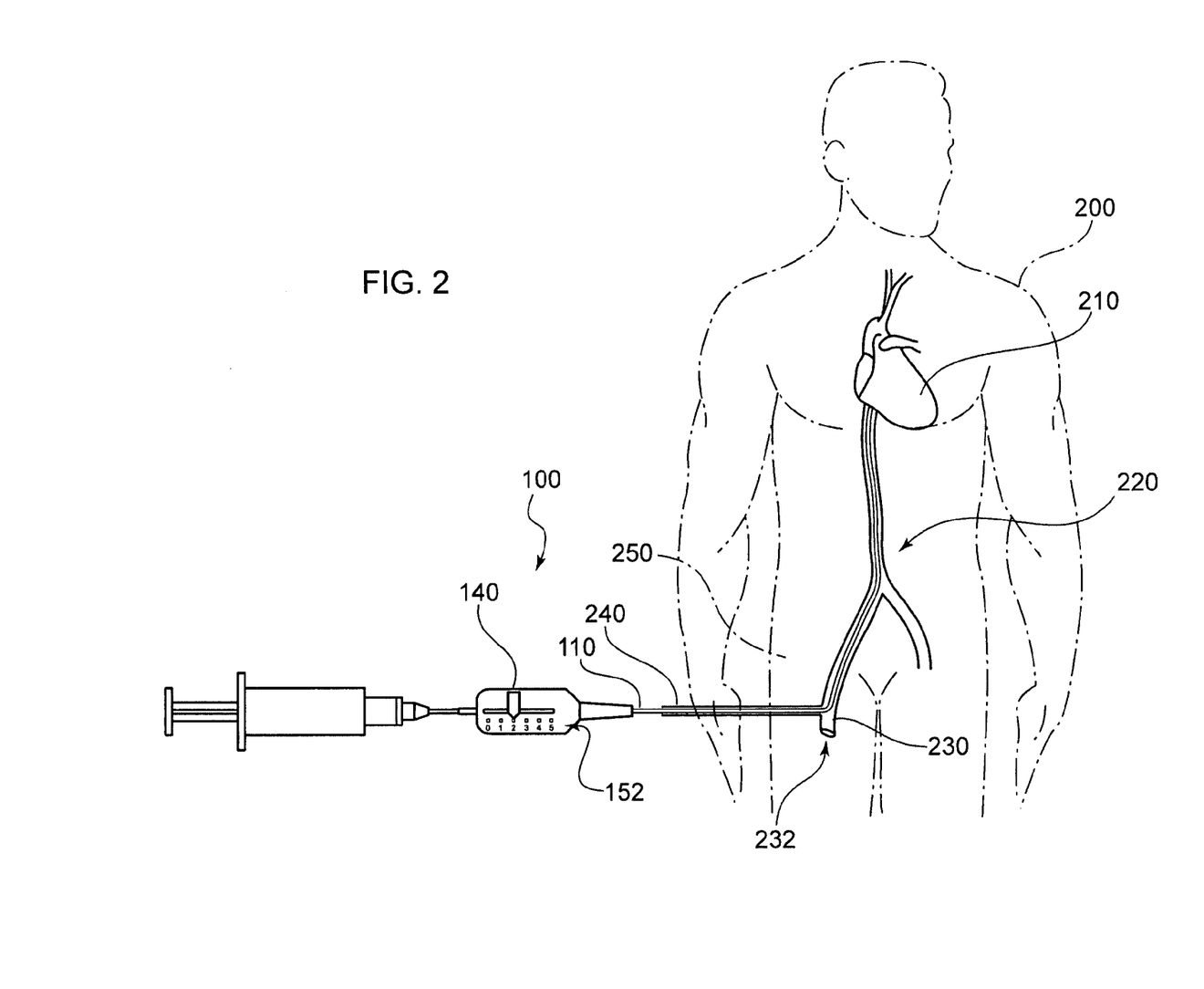
FIG. 2 is a catheter positioned within the vascular system of a patient in accord with an embodiment of the present invention.

FIG. 2 shows a catheter 100 within the vascular system 220 of patient 200. Also shown in FIG. 2 are the heart 210, blood vessels 230 and 232, access sheath 240, and leg 250 of patient 200.

As is shown, a distal end of catheter 100 may be disposed within heart 210. Specifically, a distal end of catheter 100 may be disposed against tissue of a wall of heart 210. Once positioned there, the multi-head delivery body of the present invention may be used to deliver therapeutic to the heart or other target site.

Figure 3:
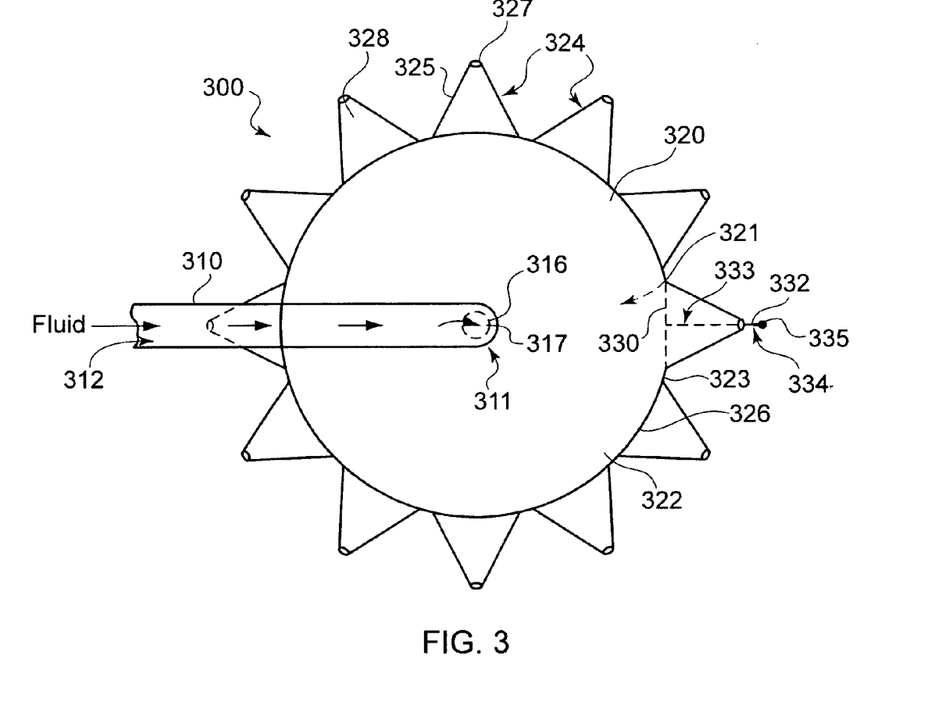
FIG. 3 is a side view of a portion of a distal end of a rotatable multi-head delivery device in accord with the an embodiment of the present invention.

FIG. 3 is a side view of a multi-head delivery device 300 in accord with an embodiment of the present invention. This device 300 as well as other devices of the present invention may be used with the catheter system 100 described above as well as with other positioning and control systems. It is preferred that these systems be steerable or otherwise controllable such that a practitioner may direct their location and position during a medical procedure. The device 300 in FIG. 3, has a first elongate shaft 310, a distal end 311, and a lumen 312. Distal end 311 may be rotably coupled to an axle 316, the axle defining a lumen 317 and co-axially aligned with the multi-head delivery body 320. Axle 316 may also be in fluid communication with lumen 312 and inner cavity 321 of the multi-head delivery body 320. Multi-head-delivery body 320 may include a first circular side 322, a second circular side (not shown), and a circular wall portion 323 extending between outer diameter edges of first circular side 322 and second circular side, the circular sides defining inner cavity 321. Multi-head delivery body 320 may also include multiple injection heads 324, which may be evenly spaced around an exterior surface of circular wall portion 323.

Embodiments of the present invention are contemplated in which multi-head delivery body 320 may have a total diameter including multiple injection heads 324 that fit within a 9 french or larger catheter. Multiple embodiments of the present invention are contemplated including the single row of injection heads 324 around circular wall portion 323 as shown in FIG. 3, multiple rows of injection heads 324 with aligned columns, and multiple rows of injection heads 324 with heads in every other row being aligned with each other. Other orientations are also plausible. Each injection head 324 may include an upwardly and inwardly extending conical wall portion 325, which may define a base opening 326 in wall portion 323 and a port 327 with a lumen 328 extending there between. Lumen 328 may have a conical shape similar to conical wall portion 325 defined by an inner surface of conical wall portion 325, with an embodiment of the present invention.

Alternative embodiments of lumen 328 are also contemplated to include, for example, a cylindrical lumen, as well as various other shaped lumens. Moreover, first elongate shaft 310 may be straight and run along one side of multi-head delivery body 320, first elongate shaft 310 may also be angled near distal end 311.

In accord with embodiments of the present invention, each injection head 324 may include a substantially circular hinged base opening cover 330 coupled to a plunger 332. The proximal end 333 of the plunger may be coupled to substantially circular hinged base opening cover 330 and a distal end 334, extending out through port 327. Cover 330 may be biased against an inner surface of circular wall portion 323 to close off opening 326 by, for example, a spring loaded hinge. Although, for reasons of clarity and ease of illustration, only one injection head 324 is illustrated with cover 330 and plunger 332, each injection head 324 may also be so configured. Moreover, proximal end 333 may also be coupled to cover 330 at a substantially 90° angle while distal end 334 may include a rounded tip 335 that may extend out past port 327. Also, regardless of the shape of lumen 328, hinged based cover 330 may be sized to provide a liquid-tight seal, thereby preferably ensuring no fluid from inner cavity 321 may escape when hinged base opening cover 330 is covering opening 326.

In FIG. 3, rounded tip 335 may have a diameter smaller than a diameter of port 327. This allows rounded tip 335 to retract through port 327. This allows rounded tip 335 to retract through port 327 and back into lumen 328 to open opening 326 when urged in the proximal direction. This may occur when rounded tip 335 is pressed against a target site. Rounded tip 335 may extend out past port 327 when not pressed against the target tissue site. Cover 330 may be biased toward the inner surface of circular wall portion 323. In general, rounded tip 335 will be sized to permit fluid within inner cavity 321 to escape through lumen 328 in injection tip 324 when rounded tip 335 is pushed back within lumen 328. Similarly, when rounded tip 335 is extended past port 327, hinged base opening cover 330 may seal substantially circular base opening 326 to prevent fluid within inner cavity 321 from escaping through lumen 328. In some embodiments the therapeutic may be under pressure from the delivery head and/or a lumen in communication with the delivery head.

Figure 4:
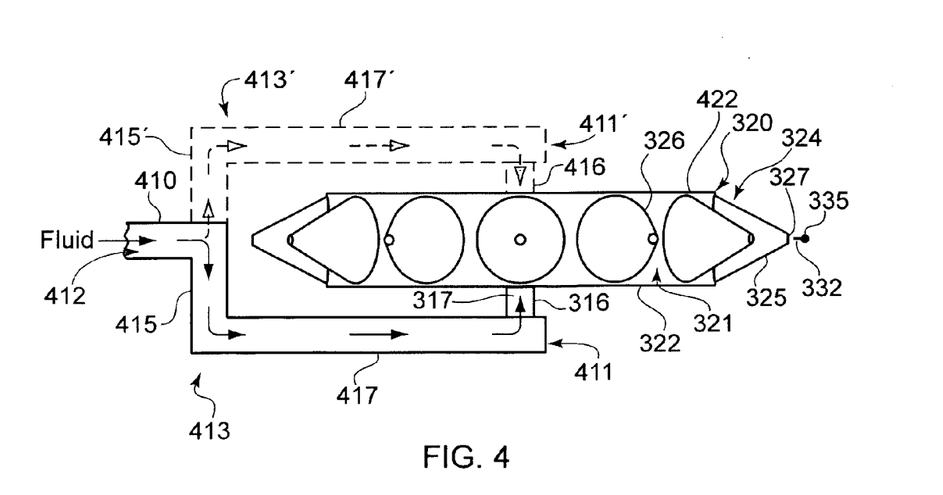
FIG. 4 is a top view of the multi-head delivery device of FIG. 3.

FIG. 4 is a top view of a portion of the multi-head delivery device of FIG. 3, in accord with an alternate embodiment of the present invention. In FIG. 4, a first elongate shaft 410 may have a proximal end (not shown) and a distal end 411 with a lumen 412 extending there between. Distal end 411 may be rotably coupled to axle 316 defining lumen 317, which may be coupled to and co-axially aligned with multi-head delivery body 320. Axle 316 may be in fluid communication with lumen 412 and inner cavity 321 within multi-head delivery body 320. In the embodiment in FIG. 4, first elongate shaft 412 may be radially aligned with multi-head delivery body 320 and may have an end section 413 including a substantially perpendicular section 415 proximal of multi-head delivery body 320. As shown in the embodiment in FIG. 4, multi-head delivery body 320 may have a single row of injection heads 324. There may be other configurations and alignments as described herein as well.

First elongate shaft 410 may have a symmetrical end section 413' (shown in phantom line). This may include a substantially perpendicular section 415', that may extend past second circular surface 422 of multi-head delivery body 320 and be coupled to a final distal section 417' of first elongate shaft 410. This distal section 417' may also substantially perpendicular to substantially perpendicular section 415' and substantially parallel to first circular surface 322 of multi-head delivery body 320. Distal end 411' may be rotably coupled to and co-axially aligned with another axle 416, which may be co-axially aligned with axle 316. Symmetrical end section 413' may also be in fluid communication with inner cavity 321. First elongate shaft may take other configurations as well.

Figure 5:
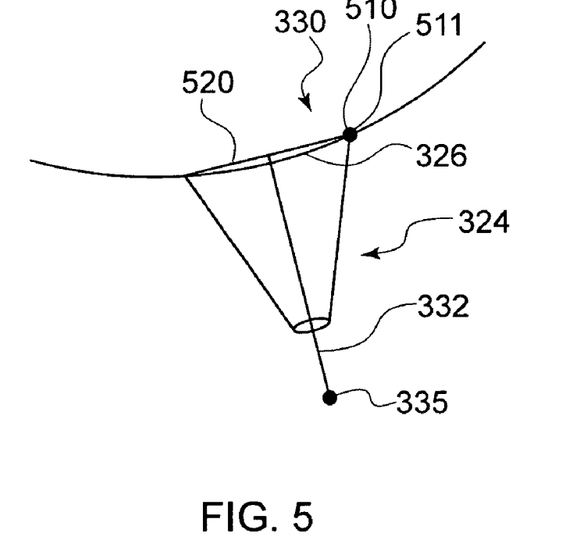
FIG. 5 is a partial cross-sectional side view of a head in a closed position, as may be employed in the present invention.

FIG. 5 is an enlarged partial cross-sectional view of an injection head in accord with an embodiment of the present invention. In FIG. 5, base cover 330 covers base opening 326 of injection head 324. Hinged base cover 330 may include a hinge 510 that may be coupled to a substantially circular plate 520 and an inner surface of circular wall portion 323 adjacent to substantially circular base opening 326. Hinge 510 may bias substantially circular plate 520 against the inner surface of circular wall portion 323 by, for example, a spring 511. In general, spring 511 may be arranged in a similar fashion to a spring in a standard mousetrap that urges the arm of the mousetrap against the base. The force of spring 511 may be sufficient to prevent substantially circular plate 520 from unsealing from the inner surface of circular wall portion 323 when multi-head delivery body 320 is rotated. In addition, substantially circular plate 520 may include a material that may form a tight liquid seal when biased against the inner surface of circular wall portion 323. For example, substantially circular plate 520 may be comprised of the material and/or include the material only on the side facing the inner surface of circular wall portion 323, where the material may include natural rubber, isoprene, urethane, latex, acrylonitrile/butadiene, cyanoacrylate, fibrin, collagen and/or silicone.

Figure 6:
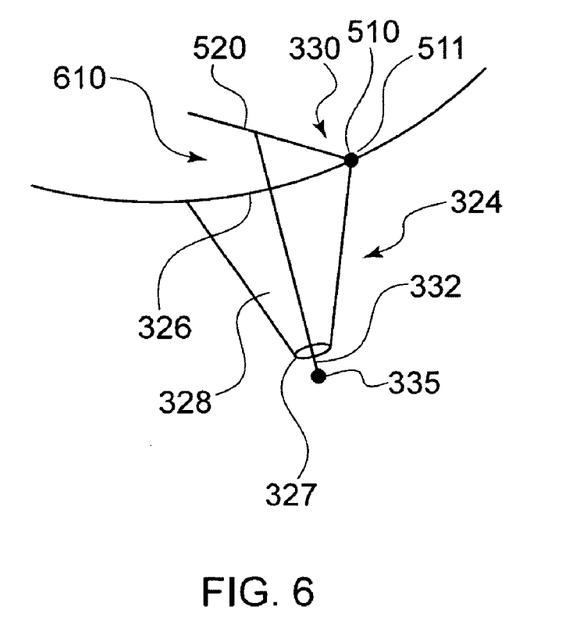
FIG. 6 is a partial cross-sectional side view of the head from FIG. 5 showing the head in an open position, as may be employed in the present invention.

FIG. 6 is an enlarged partial cross-sectional side view of a portion of a head in an open position, in accord with an embodiment of the present invention. In FIG. 6, substantially circular plate 520 may be displaced from the inner surface of circular wall portion 323 as the plunger 332 is urged in the proximal direction. This will force rounded end 335 into port 327. Displacing substantially circular plate 520 away from the inner surface of circular wall portion 323 may create a vent 610 for the fluid in inner cavity 321 to enter lumen 328 through substantially circular base opening 326 and exit through port 327. In the open position, spring 511 may be compressed so that it may exert a bias against substantially circular plate 520 to return to the closed position shown and described in FIG. 5.

Figure 21:
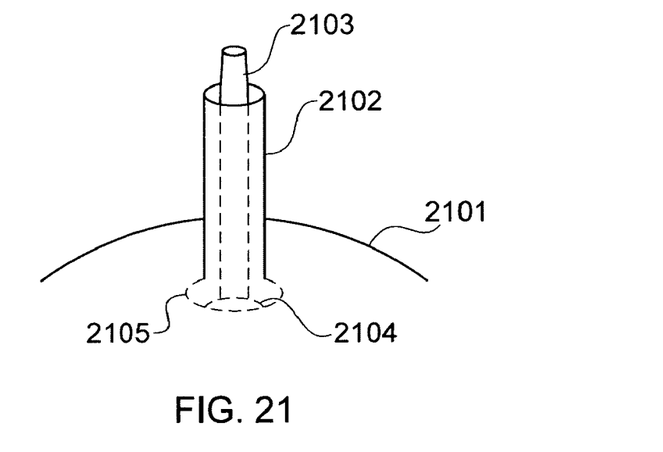
FIG. 21 is a head design in accord with the present invention.

FIG. 21 is an enlarged view of another head 2102 that may be employed by one or more of the rotatable bodies of the present invention. Like the other heads, they may be spaced and positioned in various locations and may be employed with other types of heads on the same system or device. A plunger 2103, flap 2104, biasing element 2105, and multi-head rotatable body 2101, may all be seen in this figure. The biasing element 2105 may act to keep the plunger 2103 in a closed position until the plunger is depressed.

Figure 7:
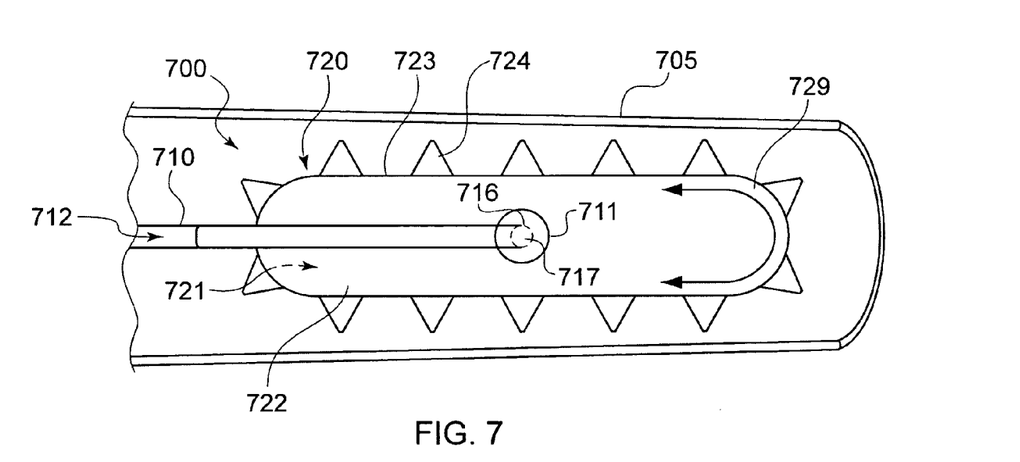
FIG. 7 is a side view of a portion of a distal end of a multi-head delivery device in accord with the present invention.

FIG. 7 is a side view of a portion of a distal end of another multi-head delivery device in accord with the present invention. In FIG. 7, a multi-head delivery device 700 may include an elongated shaft 710 having a proximal end (not shown), a distal end 711, and a lumen 712 there between. Multi-head delivery device 700 may be disposed in a catheter 705 having a proximal end, a distal end, and a lumen extending there between. Elongated shaft 710 may be rigidly coupled to and coaxially aligned with an axle 716 having a lumen 717 that may be coupled to a multi-head delivery body 720 to permit lumen 712 to be in fluid communication with an inner cavity 721 through an opening in a first side surface 722 in multi-head body 720. Multi-head body 720 may include an outer tread 723 having multiple injection heads 724 and an inner portion 729 defining inner cavity 721. Outer tread 723 may be adapted to rotate around inner portion 729 and to receive and hold fluid to be ejected from each injection head 724 either from within outer tread 723 or inner cavity 721. For example, outer tread 723, as in other embodiments, may be adapted to receive and hold fluid separate and apart from inner cavity 721, which may, itself, be inflatable to press against an inner surface of outer tread 723. In so doing, inner cavity 721 may either increase or put the fluid in outer tread 723 under pressure, which may aid in the ejection of the fluid from each injection head 724. Inner portion 729 may include an inner bladder that may be deflated to permit easy movement of multi-head body 720 through catheter 705 to a target tissue site once positioned, multi-head body 720 may be extended out of catheter 705 and inner portion 729 may be inflated/expanded to permit outer tread surface 723 to rotate around inner portion 729 and eject fluid through multiple injection heads 724. The injections head 724 may also be configured and operate in other fashions, such as those described above for FIGS. 3, 5, and 21.

The heads 724 may be sized to fit within a 9 French or larger catheter. Conversely, the multi-head delivery body 720 may also have a height and width greater than a 9 French when it is inflated. Inner portion 729 having a constant size and shape.

Figure 8:
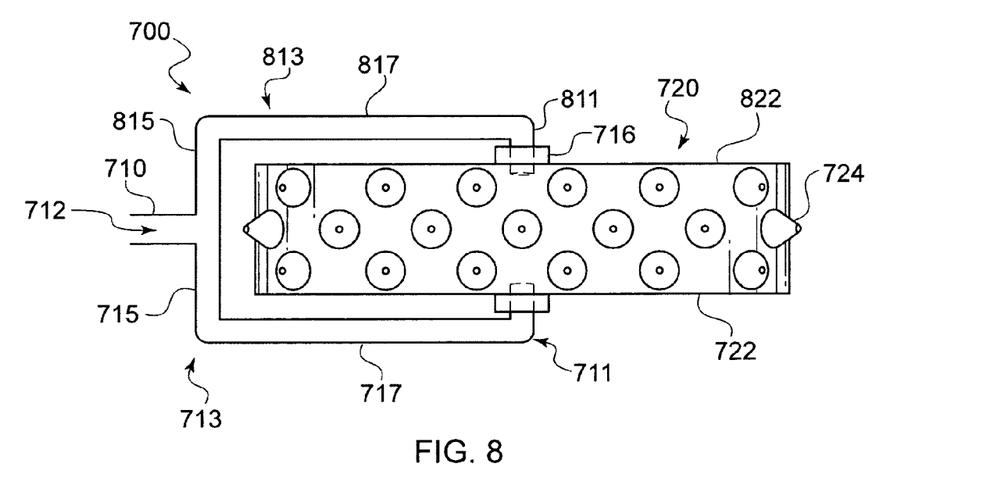
FIG. 8 is a top view of the device of FIG. 7.

FIG. 8 is a top view of multi-head delivery device of FIG. 7. As can be seen, elongate shaft 710 may be longitudinally aligned with multi-head delivery body 720 and may have a symmetrical end section 713, the end section including substantially perpendicular sections 715, 815. Sections 715 and 815 may extend past first side surface 722 and second side surface 822 and may be coupled to final distal sections 717, 817.

As also shown in FIG. 8, multi-head delivery body 720 may have multiple rows of offset injection heads 724. However, the injection heads shown elsewhere may also be used in this and other embodiments.

As shown in FIG. 8, elongate shaft 710 may be asymmetrical, similar to FIG. 4, and may only include end section 713. Distal end 711 may be rigidly coupled to and co-axially aligned with axle 716, which may be co-axially aligned with axle 316. Asymmetrical end section 713 may also be in fluid communication with inner cavity 721.

Figure 9:
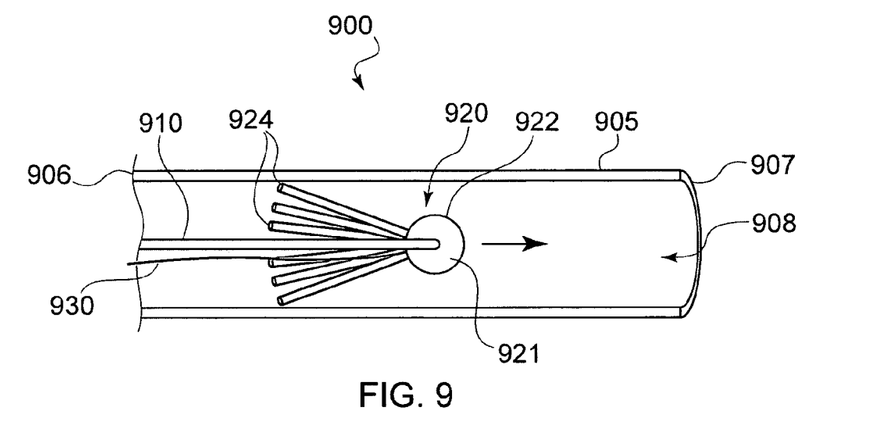
FIG. 9 is a partial cross-sectional side view of a collapsed multi-head delivery device in accord with an embodiment of the present invention.

FIG. 9 is a cross-sectional side view of a portion of the distal end of a catheter in accord with an embodiment of the present invention. In FIG. 9, a catheter 905 having a proximal end 906, a distal end 907 and a lumen 908 extending there between, is shown disposed within lumen 908 of multi-head delivery device 900. Multi-head delivery device 900 may include an elongate shaft 910 having a proximal end, a distal end, and a lumen extending there between. A multi-head delivery body 920 may have an inner cavity 921 similar to delivery body 320 from FIG. 3. It may also have multiple injection heads 924 in fluid communication with inner cavity 921. Multi-head delivers device 900 may also include a control mechanism 930 to spread and close multiple injection heads 924 of multi-head delivery body 920. For example, control mechanism 930 may include push and pull wires and/or a mechanism similar to an umbrella to permit closing the multiple injection heads 924 and to permit the transport of the multi-head delivery device 900 through lumen 908. As in FIG. 3, in FIG. 9, the lumen of elongate shaft 910 may be rotably coupled to and, co-axially aligned with inner cavity 921 in multi-head delivery body 920.

Figure 10:
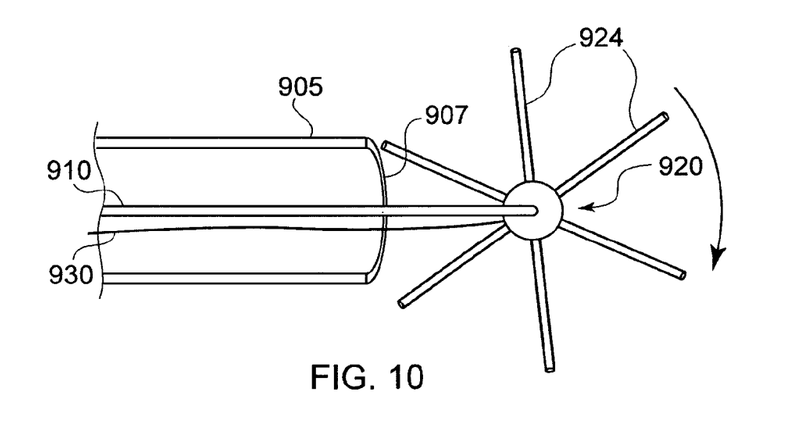
FIG. 10 is a partial cross-sectional side view of the multi-head delivery device of FIG. 9 in an expanded position, also in accord with the present invention.

FIG. 10 is a cross-sectional side view of the distal end of the catheter and multi-head delivery device of FIG. 9. In FIG. 10, the multi-head delivery body extends past the distal end of the catheter and is shown fully open. As can be seen, the multi-head delivery body 920 may be extended past distal end 907 of catheter 905 and multiple thin injection heads 924 may be extended using control mechanism 930. Moreover, multi-head delivery body 920 may rotate around distal end 911 of elongate shaft 910 and may receive fluid from inner cavity 921. This fluid may be ejected out a distal end of each injection head 924.

Figure 11:
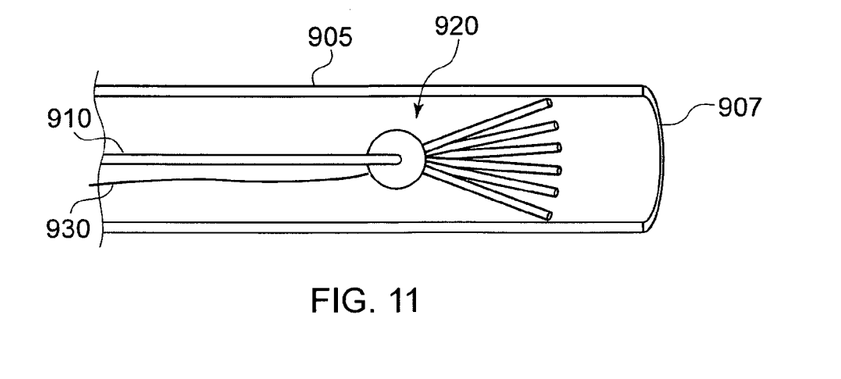
FIG. 11 is a partial cross-sectional side view of the multi-head delivery device of FIG. 9 with the multi-head body retracted back into the distal end of the catheter, also in accord with the present invention.

FIG. 11 is a cross-sectional side view of a portion of the distal end of the catheter and the multi-head delivery device from FIG. 9. In FIG. 11 the multi-head delivery body is retracted back into the distal end of the catheter so that it may move toward the proximal end of the catheter. In FIG. 11, multi-head delivery body 920 may be retracted back into distal end 907 of catheter 905 and multiple thin injection heads 924 may be collapsed in the opposite direction of FIG.

9, which is similar to an umbrella that has been opened past the desired normal open position. Multiple injection heads 924 may be designed to permit movement in this opposite direction to ease movement of the multi-head delivery body 920 back into distal end 907. In another embodiment of the present invention, control mechanism 930 may also permit closing the 924 back into the configuration shown in FIG. 9. However, bringing multi-head delivery body 920 back into distal end 907 of catheter 905 in this position may be more difficult than in the configuration shown in FIG. 11.

Figure 12:
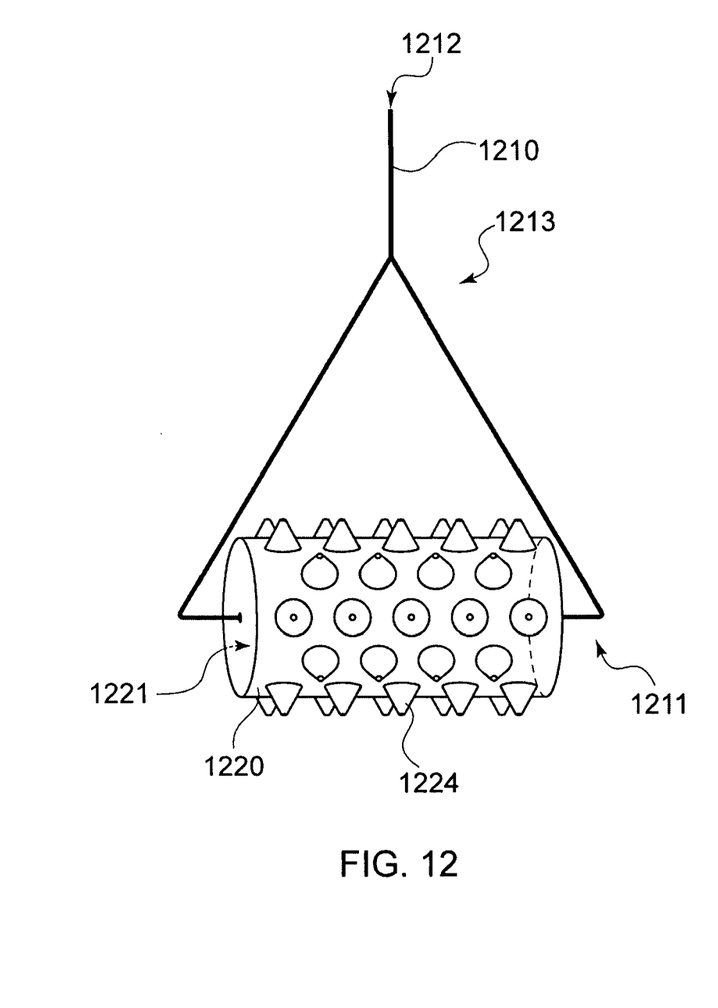
FIG. 12 is a perspective view of a distal end of another multi-head delivery device, also in accord with the present invention.

FIG. 12 is a perspective view of a distal end of a multi-head delivery device in accord with an embodiment of the present invention. In FIG. 12, a multi-head delivery device 1200 along with an elongate shaft 1210, a distal end 1211, a lumen 1212, a multi-part delivery body 1220, an inner cavity 1221, injection heads 1224, and exterior surface 1223 may all be seen. Multiple injection heads 1224 may be configured similarly to those described in FIGS. 3-6 and 21. Distal end 1211 may include a semi-rigid and/or rigid symmetrical forked section 1213 that may be rotably coupled to and co-axially aligned with an axis of multi-head delivery body 1220. Embodiments of multi-head delivery body 1220 are also contemplated in which the outer diameter of multi-head delivery body 1220 may fit within a 9 french or larger catheter and the length of multi-head delivery body 1220 may be approximately 1 cm. Embodiments of multi-head delivery body 1220 are also contemplated in which multi-head delivery body 1220 may be moved longitudinally through a catheter. For example, multi-head delivery body 1220 may need to be enclosed in a sheath (not shown) to help hold multi-head delivery body 1220 and forked section 1213 in a contracted position. The sheath may help to prevent the injection heads 1224 from catching on and damaging a lumen of the catheter through which multi-head delivery body 1220 may be moved.

Upon extending multi-head delivery body 1220 past a distal end of the catheter, the sheath may be removed, and forked section 1213 may unfold as shown in FIG. 12. Once multi-head delivery body 1220 has been positioned over a target tissue site, it may be rolled across the target tissue site to deliver therapeutic through injection heads 1224. After delivering the therapeutic, multi-head delivery body 1220 may be retracted back into a distal end of the catheter. The multi-head delivery body 1220 may also be retracted back into a distal end of the sheath so that multi-head delivery body 1220 may be removed from a patient within or outside of the catheter.

Figure 13:
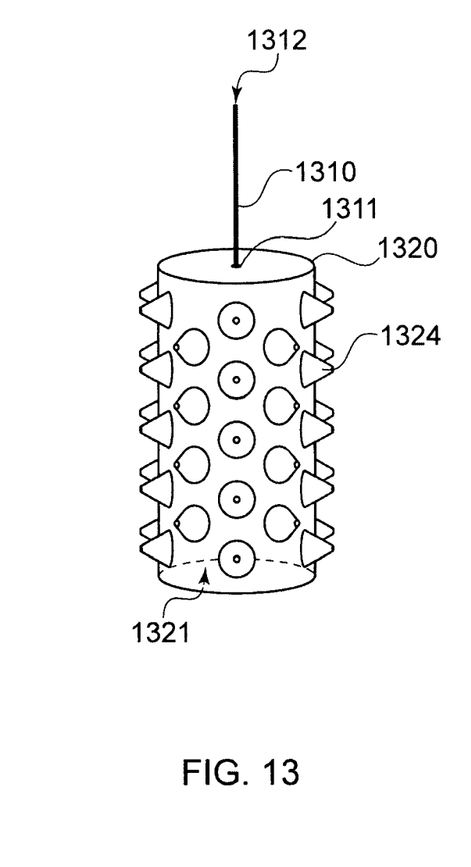
FIG. 13 is a perspective view of another multi-head delivery device, also in accord with the present invention.
Figure 14:
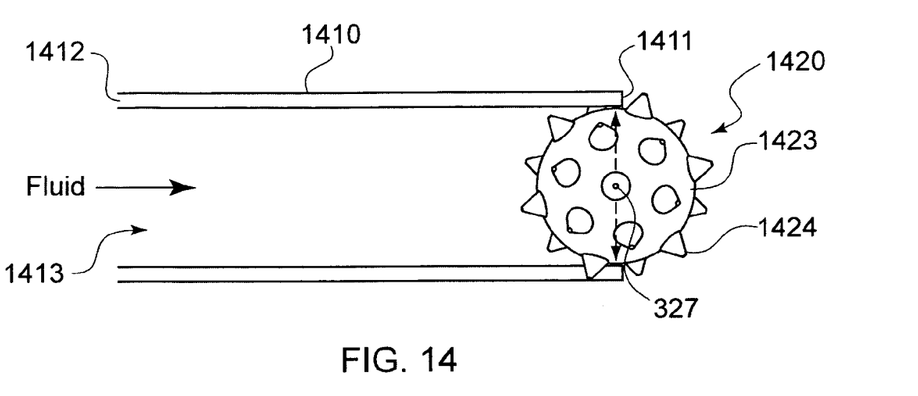
FIG. 14 is a partial cross-sectional view of another multi-head delivery device, also in accord with the present invention.
Figure 15:
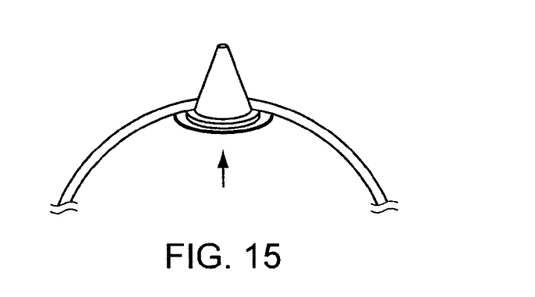
FIG. 15 is a partial cross-sectional view of the rotatable body of the multi-head delivery device of FIG. 14.
Figure 16:
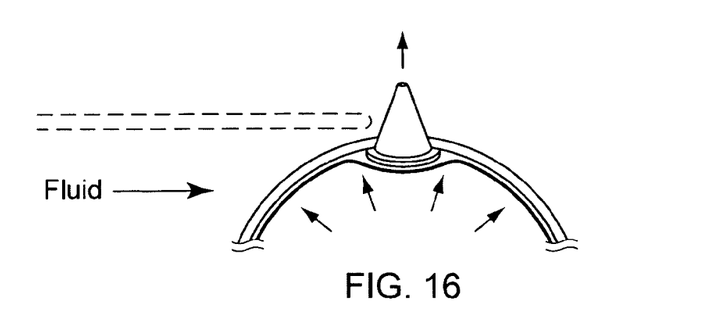
FIG. 16 is a partial cross-sectional view of the rotatable body of FIG. 15 with a head in a fully extended position.
Figure 17:
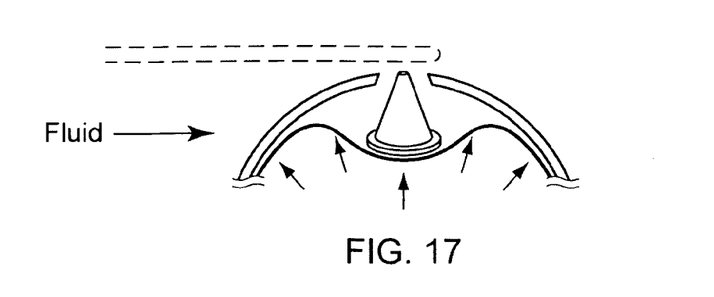
FIG. 17 is the partial cross-sectional view of the rotatable body of FIG. 15 with the head in a retracted position.

In FIG. 13, the multi-head delivery device 1300 may include an elongate shaft 1310, a distal end 1311, a lumen 1312, a multi-head delivery body 1320, an inner cavity 1321, and multiple injection heads 1324 spaced in a substantially even pattern around an exterior surface 1323 of multi-head delivery device 1320. Multiple injection heads 1324 may be configured and operate similar to those described in FIGS. 3-6 and 21. In the present embodiment, elongate shaft 1310 may be rotably coupled to and co-axially aligned with multi-head delivery body 1320.

Embodiments of multi-head delivery body 1320 may include a multi-head delivery body that may be moved longitudinally through a catheter. For example, multi-head delivery body 1320 may need to be enclosed in a sheath (not shown) to prevent multiple injection heads 1324 from catching on and damaging a lumen of the catheter through which multi-head delivery body 1320 may be moved. Upon extending multi-head delivery body 1320 past a distal end of the catheter, the sheath may be removed, if present, and multi-head delivery body 1320 may be positioned over a target tissue site and rolled across the target tissue site to deliver a therapeutic through multiple injection heads 1324 that may be provided by lumen 1312 of elongate shaft 1310. After delivering the therapeutic, multi-head delivery body 1320 may be retracted back into a distal end of the catheter using, for example, elongate shaft 1310 to pull multi-head delivery body 1320 back into the catheter and then remove the catheter and multi-head delivery body 1320 together. In the sheath embodiment, the multi-head delivery body 1320 may also be retracted back into a distal end of the sheath so that multi-head delivery body 1320 may be removed with or without the catheter.

Figure 18:
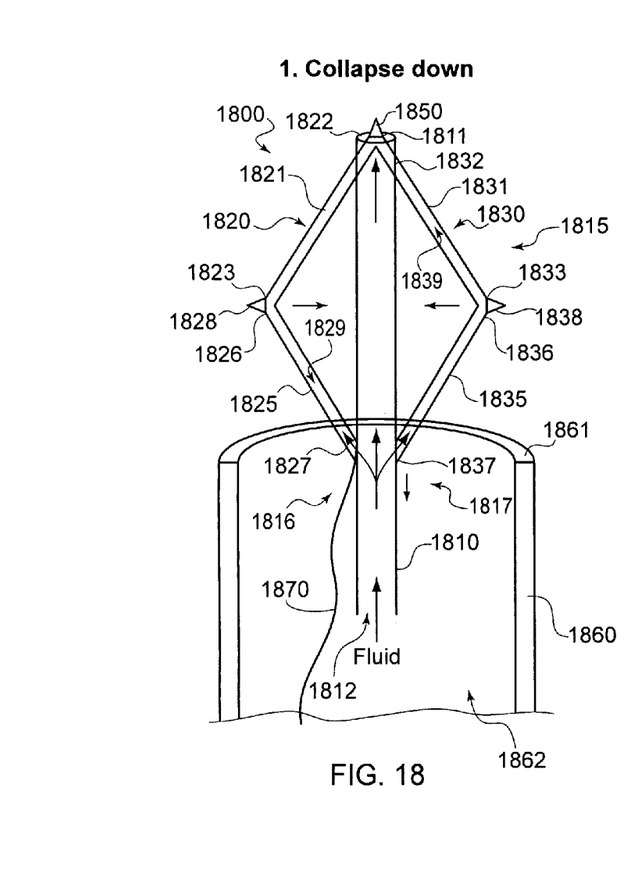
FIG. 18 is a partial side view of a portion of a distal end of another multi-head delivery device, also in accord with the present invention.

FIG. 18 is a side view of a portion of a distal end of a catheter with an alternative multi-head delivery body. In FIG. 18, expandable multi-head delivery device 1800 may include an elongated shaft 1810 having a proximal end, a distal end 1811 and a lumen 1812 extending there between. It may also include a symmetrical, collapsible multi-head delivery body 1815 having a first arm 1820 and a second arm 1830. Lumen 1812 may be in fluid communication with the proximal end of elongated shaft 1810. First arm 1820 may include a distal arm section 1821 having a distal end 1822 and a proximal end 1823. First arm distal end 1822 may be pivotally coupled to elongated shaft distal end 1811. First arm 1820 may also include a proximal arm section 1825 having a distal end 1826 pivotally coupled to distal arm section proximal end 1823 to form a side needle 1828 and a proximal end 1827 slidingly coupled to a section 1816 of elongated shaft 1810. First arm 1820 may also include a lumen 1829 extending between first arm distal end 1822 and second arm proximal end 1827, the lumen in fluid communication with elongated shaft lumen 1812. Second arm 1830 may include a distal arm section 1831 having a distal end 1832 and a proximal end 1833. Second arm distal end 1832 may be pivotally coupled to elongated shaft distal end 1811 to form a distal needle 1850. Second arm 1830 may also include a proximal arm section 1835 having a distal end 1836 pivotally coupled to distal arm section proximal end 1833 to form a side needle 1838. Second arm may also have a proximal end 1837 slidingly coupled to a section 1817 of elongated shaft 1810 near elongated shaft distal end 1811. Second arm 1830 may also include a lumen 1839 extending between first arm distal end 1832 and second arm proximal end 1837 in fluid communication with elongated shaft lumen 1812.

As can be seen in FIG. 18 elongated shaft 1810 may be disposed within a catheter 1860 to permit elongated shaft 1810 to be moved to a target tissue site within catheter 1860 thus preventing needles 1828, 1838, and 1850 from substantially injuring tissue in a patient before the distal end of elongated shaft 1810 can be positioned near the target tissue site. As seen in FIG. 18, the distal end of elongated shaft 1810 including collapsible multi-head delivery body 1815 is extended out past catheter 1860 distal end 1861 and illustrates collapsible multi-head delivery body 1815 in a partially open position. Movement lines indicate the collapsible multi-needle structure 1815 is being closed. In the closed position, collapsible multi-head delivery body 1815 may abut an exterior surface of elongated shaft 1810 to permit easy movement of elongated shaft 1810 through catheter lumen 1862. In the closed position elongated shaft lumen 1812 may remain in fluid communication with first arm lumen 1829 and second arm lumen 1839. This may be done, for example, via proximal end 1827 and/or proximal end 1837 and distal end 1822 and/or distal end 1832. Alternatively, elongated shaft lumen 1812 may not remain in fluid communication with first arm lumen 1829 and second arm lumen 1839 in the closed position.

In accord an embodiment of the present invention a control mechanism may be implemented similar to an umbrella opening and closing mechanism that may be actuated from the proximal end of elongated shaft 1810 to control the opening and closing of collapsible multi-head delivery body 1815. For example, one or more push/pull wires may be attached to collapsible multi-head delivery body 1815 to permit the opening and closing of collapsible multi-head delivery body 1815 by pushing/pulling one or more of the push/pull wires. Alternatively, collapsible multi-head delivery body 1815 may be biased toward the open position by, for example, a spring-loaded umbrella mechanism that may be opened by a control mechanism 1870 to permit collapsible multi-head delivery body 1815 to open. Similarly, collapsible multi-head delivery body 1815 may open upon being extended past the distal end of catheter 1860 a predetermined distance. Similarly, collapsible multi-needle structure 1815 may also be closed by control mechanism 1870. Opening may be accomplished by releasing the spring-loaded mechanism and closing may be accomplished by pulling a proximal end of push/pull wire 1870 at the proximal end of catheter 1860 in the proximal direction. Alternatively, fluid pressure (positive or negative) may be used to open or close the device.

Although the embodiment shown in FIG. 18 may only show two arms 1820, 1830, other embodiments are contemplated in which three or more arms, may be implemented.

Figure 19:
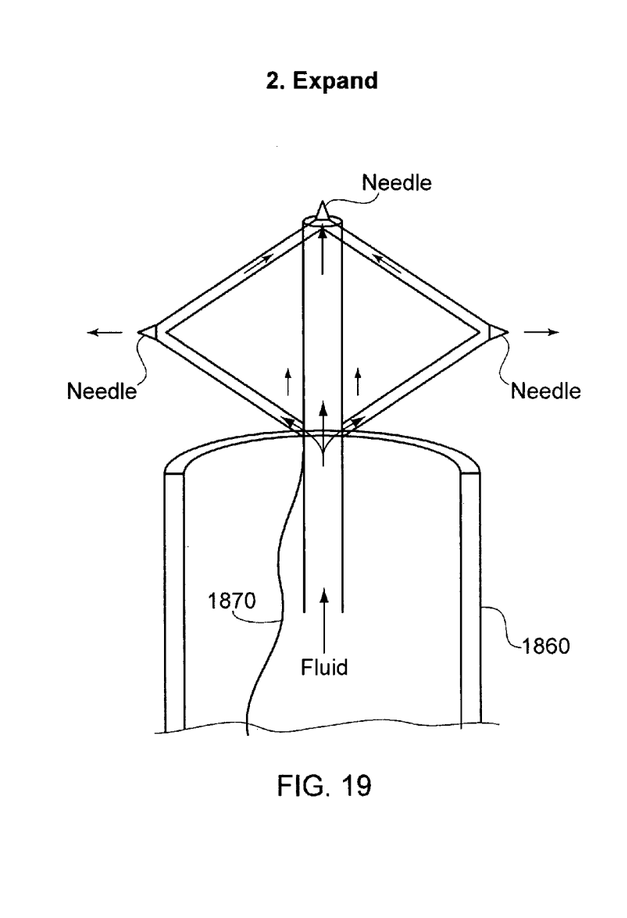
FIG. 19 is a partial side view of the multi-head delivery device of FIG. 18 in an expanded position.

FIG. 19 is a side view of the portion of the distal end of the catheter of FIG. 18 with the expandable multi-tip injection structure in an expanded position. In FIG. 19, the extended position collapsible multi-head delivery body 1815 may be urged distally to inject a target tissue site with needle 1850. Likewise, collapsible multi-head delivery body 1815 may be urged laterally in one or both directions to inject tissue sites with needle 1828 and/or needle 1838.

Figure 20:
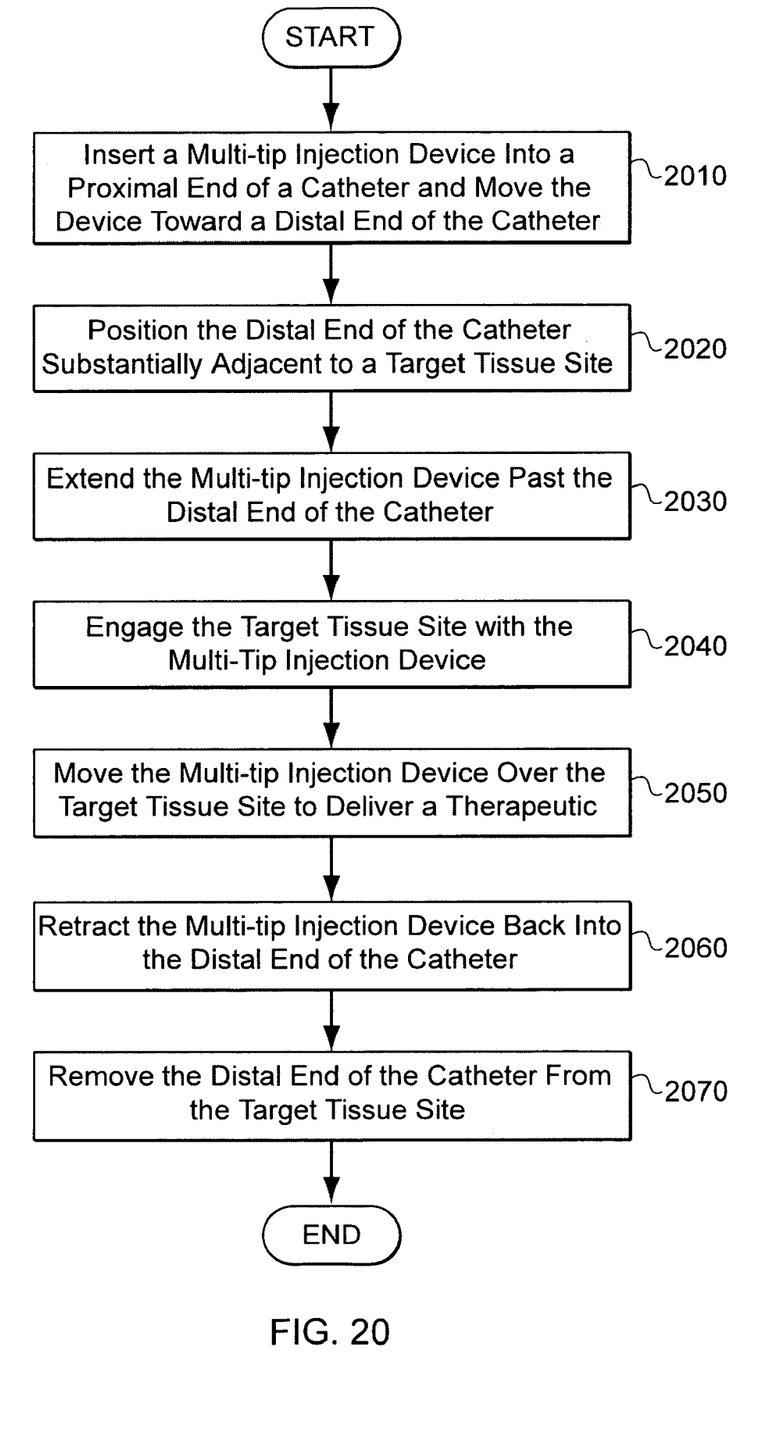
FIG. 20 is a flow diagram of a method of using a multi-head delivery device in accord with the present invention.

FIG. 20 is a flow diagram illustrating a method in accordance with an embodiment of the present invention. In FIG. 20, the method may include inserting (2010) a multi-head delivery device into a catheter and moving the multi-head delivery device to a distal end of the catheter. The method may also include positioning (2020) the distal end of the catheter substantially adjacent to a target tissue site within a patient and extending (2030) the multi-head delivery device past the distal end of the catheter. The method may further include engaging (2040) the target tissue site with the multi-head delivery device heads of the multi-head delivery device into the target tissue site, and moving (2050) the multi-head delivery device over the target tissue site to deliver a therapeutic to the target tissue site. The method may also further include retracting (2060) the multi-head delivery device back into the distal end of the catheter and removing (2070) the distal end of the catheter from the target tissue site. Although the method of FIG. 3 described above may appear to indicate an exact order of execution of the elements of the method, it is not intended as such.

For example, in an embodiment of the present invention, the operation of multi-head delivery body 320 of FIG. 3 may include inserting (2010) multi-head delivery body 320 into lumen 116 at the proximal end of catheter 100 of FIG. 1, and moving multi-head delivery body 320 to a distal end of catheter 100. The method may also include positioning (2020) the distal end of catheter 100 substantially adjacent to a target tissue site within a patient and extending (2030) multi-head delivery body 320 past the distal end of catheter 100. The method may further include engaging (2040) the target tissue site with multi-head delivery body 320, for example inserting some number of multiple injection heads 324 of multi-head delivery body 320 into the target tissue site, and moving (i.e., rolling) (2050) multi-head delivery body 320 over the target tissue site to deliver a therapeutic to the target tissue site. This may include rolling (2050) multi-head delivery body 320 across the target tissue site once as well multiple times to provide the coverage deemed necessary by the practitioner. The method may still further include retracting (2060) multi-head delivery body 320 back into the distal end of catheter 100 and removing (2070) the distal end of catheter 100 from the target tissue site. In the present embodiment, the therapeutic may be introduced into lumen 312 of elongated shaft 310 either prior to or after inserting (2010) multi-head delivery body 320 into catheter 100, extending (2030) multi-head delivery body 320 past the end of catheter 100 or engaging (2030) the target tissue site.

Figure 22:
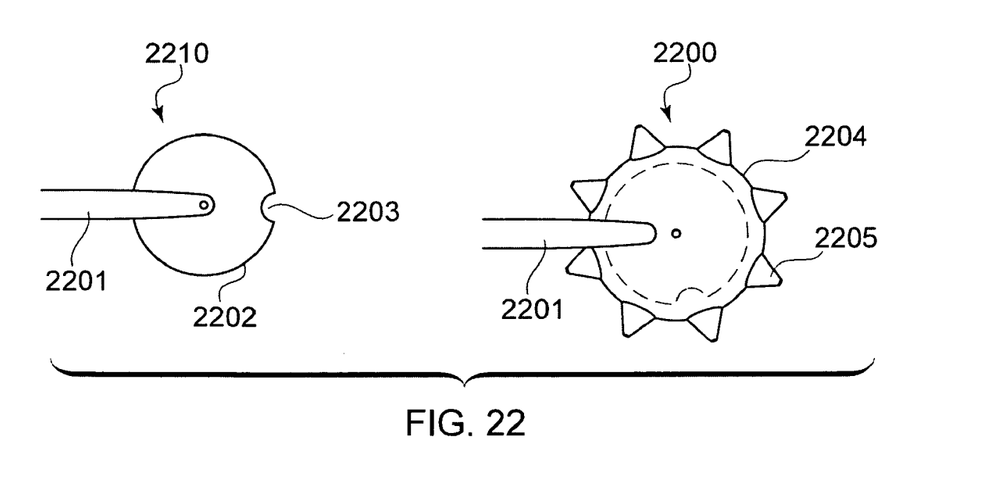
FIG. 22 is a multi-head delivery device that employs an inner rotatable disc valve in accord with an embodiment of the present invention.

FIG. 22 is another alternative embodiment of the present invention. In this embodiment the multi-head delivery device 2200 includes an outer disc 2204 and an inner disc 2202; the inner disc having a port 2203 and the outer disc having several delivery heads 2205. Both the inner disc and the outer disc may rotate about the support 2201. When the port 2203 of the inner disc aligns with a delivery head 2205, therapeutic within the inner disc may be released through the port 2203 and the head 2205. This therapeutic may be stored within the disc as well as be supplied to the inner disc through the support 2201.

A detailed description of embodiments of catheter assemblies that may be used in embodiments of the present invention may be found in co-pending U.S. patent application Ser. No. 09/635,083, filed by the same assignee on Aug. 8, 2000, and entitled "Catheter Shaft Assembly."

The term "therapeutic agent" as used herein may include one or more "therapeutic agents" or "drugs." The terms "therapeutic agents" and "drugs" are used interchangeably herein and may include pharmaceutically active compounds, nucleic acids with and without carrier vectors such as lipids, compacting agents (such as histones), virus (such as adenovirus, andenoassociated virus, retrovirus, lentivirus and α-virus), polymers, hyaluronic acid, proteins, cells and the like, with or without targeting sequences.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N,N',N'-tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as lisidomine, molsidomine, L-arginine, NOcarbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; and any combinations and prodrugs of the above include statins, β-blockers, and ACE inhibitors.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMPs"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homdimers, heterodimers or combinations thereof, alone or together with other molecules. Alternatively, or in addition, molecules capable of inducing an upstream or downstream effect of a BMP can be provided. Such molecules include any of the "hedghog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered.

Any of the therapeutic agents may be combined to the extent such combination is biologically compatible.

Any of the above mentioned therapeutic agents may be incorporated into a polymeric coating on the medical device or in the medical device. The polymers may be biodegradable or non-biodegradable. Non-limiting examples of suitable non-biodegradable polymers include polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyisobutylene copolymers and styrene-isobutylene-styrene block copolymers such as styrene-isobutylene-styrene tert-block copolymers (SIBS); polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly(lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

In a preferred embodiment, the polymer is polyacrylic acid available as HYDROPLUS® (Boston Scientific Corporation, Natick, Mass.), and described in U.S. Pat. No. 5,091,205, the disclosure of which is incorporated by reference herein. In a more preferred embodiment, the polymer is a co-polymer of polylactic acid and polycaprolactone.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating on the medical device is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

The present invention may include designs that use catheters manufactured by Boston Scientific of Natick, Mass. including the Stiletto™ catheter. Likewise, embodiments of the present invention may also use catheters with and without hoods, with and without an electrode sensor tip, and with combinations of the above-described features in catheters with and without deflectable tips.

Still further, the present invention may include a body with multiple heads spaced over an exterior surface of the body. The multiple heads may be spaced evenly, randomly and/or in a specific pattern over on exterior surface of the body. For example, the multi-head delivery device may include a cylindrically shaped body with the multiple heads being arranged in evenly spaced longitudinal rows and evenly spaced circumferentially arranged columns or the multiple heads may be arranged in evenly spaced and offset longitudinal rows so that heads in every other row may be aligned with each other. The multiple heads may provide for the injection or other delivery of therapeutic from within the multi-head delivery device as well as be made of a solid therapeutic that may break off as each head is inserted into a target area.

The multi-head delivery device may permit the rapid deployment of therapeutic agents over a tissue area by rolling, for example, the device across the area. This may be especially useful when a large area of tissue needs to be dosed with the therapeutic agent while the multi-head device is positioned inside a patient's body. This can reduce procedural time and costs due to the large tissue area that may be quickly treated with embodiments of the present invention.

Although the present invention has been disclosed in detail, it should be understood that various changes, substitutions, and alterations may be made herein, the present invention is intended to cover various modifications of each embodiment as well as between embodiments. Other examples are readily ascertainable from the above description and may be made without departing from the spirit and scope of the present invention.

What is claimed is:

1. A therapeutic delivery device compromising:
   a steerable elongated member sized for insertion into a body of a patient;
   a rotatable therapeutic delivery body rotatably supported by the elongated member; and
   a cover surrounding at least a portion of the elongated member, the elongated member slidable within the cover;
   the delivery body free to rotate about at least one axis of rotation extending in an axial direction,
   the delivery body having at least a first therapeutic delivery port,
   the delivery body sized for insertion into a body of a patient,
   the first therapeutic delivery port extending in a first direction outwardly from the axial direction, the first direction being different than the axial direction of the axis of rotation,
   the delivery body adapted to be rotated about the axis of rotation from a first position in which the first therapeutic delivery port is at a first angular position about the axis of rotation to a second position in which the first therapeutic delivery port is at a second angular position about the axis of rotation.

2. The therapeutic delivery device of claim 1 wherein the first therapeutic delivery port is in fluid communication with a lumen within the delivery body.

3. The therapeutic delivery device of claim 1 wherein the elongated member further compromises an axle about which the delivery body is rotatably supported.

4. The therapeutic delivery device of claim 1 wherein the delivery body is spherical.

5. The therapeutic delivery device of claim 1 wherein the delivery port is retractable into the delivery body.

6. The therapeutic delivery device of claim 1 wherein the delivery body comprises a track belt and wherein the delivery port is positioned on the track belt.

7. The therapeutic delivery device of claim 5 wherein the delivery body is spherical and wherein the delivery port is in an extended position in a first orientation and is in a retracted position in a second orientation.

8. The therapeutic delivery device of claim 1 wherein the first therapeutic delivery port has a piercing surface, and wherein the first therapeutic delivery port is affixed to the delivery body.

9. The therapeutic delivery device of claim 1 wherein the delivery body is coated with a therapeutic.

10. The therapeutic delivery device of claim 1 wherein the first therapeutic delivery port is coated with a therapeutic.

11. The therapeutic delivery device of claim 1 wherein the delivery body is an expandable balloon.

12. The therapeutic delivery device of claim 1 wherein the cover is an endoscope.

13. The therapeutic delivery device of claim 1 wherein the delivery body includes an expandable bladder, the bladder sized to force therapeutic from the delivery body through the delivery port as the bladder expands within the delivery body.

14. The therapeutic delivery device of claim 1 wherein the delivery body is cylindrical, and wherein an outer circumference of the delivery body comprises a plurality of delivery ports, at least one of the delivery ports have a piercing tip.

15. A therapeutic delivery device comprising:
   a steerable elongated member sized for insertion into a body of a patient;
   a rotatable therapeutic delivery body rotatably supported by the elongated member; and
   a base opening cover moveable between an opened position and a closed position,
   the delivery body free to rotate about at least one axis of rotation extending in an axial direction,
   the delivery body having at least a first therapeutic delivery port, the delivery body sized for insertion into a body of a patient, the first therapeutic delivery port extending in a first direction outwardly from the axial direction, the first direction being different than the axial direction of the axis of rotation, the delivery body adapted to be rotated about the axis of rotation from a first position in which the first therapeutic delivery port is at a first angular position about the axis of rotation to a second position in which the first therapeutic delivery port is at a second angular position about the axis of rotation, the base opening cover positioned to prevent flow of therapeutic from within the delivery body to a delivery port.

16. The therapeutic delivery device of claim 1 wherein one or more of the delivery ports contains a plunger extending from within the delivery port, to outside of the delivery port.

17. The therapeutic delivery device of claim 16 wherein the plunger is coupled to a base opening cover positioned between the delivery body and the delivery port.

18. The therapeutic delivery device of claim 16 wherein the plunger has a blunted tip.

19. The therapeutic delivery device of claim 1 wherein an end of the elongated member supporting the delivery body has an axle, the axle passing completely through the delivery body.

20. The therapeutic delivery device of claim 15 wherein a surface of the base opening cover is faced with a fibrin.

21. The therapeutic delivery device of claim 15 wherein a surface of the base opening cover is faced with a silicon.

22. The therapeutic delivery device of claim 15 wherein a surface of the base opening cover is faced with cyanoacrylate.

23. The therapeutic delivery device of claim 15 wherein a surface of the base opening cover is faced with a liner material.

24. The therapeutic delivery device of claim 1 wherein the delivery head is conically shaped.

25. The therapeutic delivery device of claim 1 wherein the delivery body comprises a second therapeutic delivery port extending in a second direction outwardly from the axial direction, and wherein when the delivery body is rotated about the axis of rotation from the first position to the second position to move the first therapeutic delivery port away from the first angular position about the axis of rotation, the second therapeutic delivery port is moved into the first angular position about the axis of rotation.

26. The therapeutic delivery device of claim 1 wherein the first direction is orthogonal to the axial direction.

27. The therapeutic delivery device of claim 25 wherein the first and second directions are orthogonal to the axial direction.

28. The therapeutic delivery device of claim 1 wherein the delivery body is in the shape of a wheel and the first therapeutic delivery port extends in a radial direction away from the axis of rotation.

29. The therapeutic delivery device of claim 25 wherein the delivery body is in the shape of a wheel and the first and second therapeutic delivery ports extend in radial directions away from the axis of rotation.

30. The therapeutic delivery device of claim 1 wherein the delivery body is moveable from a first position to a second position, the first position located within the cover, the second position located beyond a distal end of the cover.

31. The therapeutic delivery device of claim 30 wherein the cover is a catheter.

32. A therapeutic delivery device comprising:

a steerable elongated member sized for insertion into a body of a patient; and a rotatable therapeutic delivery body rotatably supported by the elongated member;

the delivery body free to rotate about at least one axis of rotation extending in an axial direction, the delivery body having at least a first therapeutic delivery port being defined by a delivery head, the delivery body sized for insertion into a body of a patient, the first therapeutic delivery port extending in a first direction outwardly from the axial direction, the first direction being different than the axial direction of the axis of rotation, the delivery head further comprising a plunger slidable within the delivery head, the plunger coupled to a plate movable from a first position to a second position, the delivery body adapted to be rotated about the axis of rotation from a first position in which the first therapeutic delivery port is at a first angular position about the axis of rotation to a second position in which the first therapeutic delivery port is at a second angular position about the axis of rotation.

* * * * *